United States Patent [19]

Saville

[11] Patent Number: Plant 6,951

[45] Date of Patent: Jul. 25, 1989

[54] MINIATURE ROSE PLANT NAMED SAVADEE

[75] Inventor: F. Harmon Saville, Newburyport, Mass.

[73] Assignee: Nor'East Miniature Roses, Inc., Rowley, Mass.

[21] Appl. No.: 230,800

[22] Filed: Aug. 10, 1988

[51] Int. Cl.[4] ..... A01H 5/00

[52] U.S. Cl. ..... Plt./7

[58] Field of Search ..... Plt./7

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and unusual yellow and orange-red miniature rose.

1 Drawing Sheet

SUMMARY OF THE INVENTION

The present invention relates to a new and distinct variety of rose plant of the miniature rose class, which was originated by my crossing as seed parent the variety known as "Zorina" (U.S. Plant Pat. No. 2,321) and as pollen parent an unnamed, unpatented seedling of my creation. The varietal denomination of this new rose is "Savadee".

Among the novel characteristics possessed by this new variety which distinguishes it from its parents and all other varieties of which I am aware are its unusual yellow and orange flowers in this class of rose. Flower are long lasting on the plant and after cutting. Asexual reproduction by propagation by cuttings of the new variety as performed in San Bernardino County, Calif. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and as depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "16B" is plate 16B of The Royal Horticultural Society Colour Chart.

Parentage: Seedling.

*Seed parent.*—"Zorina".

*Pollen parent.*—Unnamed seedling.

Class: Miniature.

The following observations are made of specimens grown outdoors in San Bernardino County, Calif., during the month of April.

FLOWER

Blooming habit: Nearly continuous.

A. Bud:

(1) *Size.*—Medium.

(2) *Form.*—High centered, flat on top.

(3) *Color.*—As sepals divide, bud color is near 16B flushed with 32B.

(4) *Sepals.*—Relatively smooth, longer than bud.

(5) *Peduncle.*—Length — about $\frac{3}{4}$ to 1-inch. Aspect — straight. Strength — erect. Color — near 144B.

B. Bloom:

(1) *Size.*—Average size when fully expanded — about $1\frac{1}{8}$ inch.

(2) *Borne.*—Singly, one to a stem and in sprays of 3 to 8 blooms.

(3) *Forms.*—High centered at first, becoming flat. Outer petals reflex and quill to points; inner petals roll under, becoming ruffled.

(4) *Petalage.*—Number of petals under normal conditions — about 24 to 28.

(5) *Color.*—After sepals fall and petals unfurl, predominant flower color viewing petals' top surface is near 12B to D flushed with 32B with deeper tones, near 34A, at some apices. Petal under surfaces tend to deeper yellow hues, near 16B but become flushed with near 32B to 33B toward outer portion of petals. Flower coloring at centers where petals bunch appears near 32A to 32B and yellow coloring predominates on petals near point of petal attachment. The lower segment of petal top surfaces extending toward point of petal attachment appears more distinctly yellow on both top and under surfaces. The petal undersurface is predominantly yellow imbued with orange red and petal top surface displays some veining. Orange and orange red tones become pink and reddish upon aging.

C. Petals:

(1) *Texture.*—Thick.

(2) *Appearance.*—Inside velvety and outside satiny.

(3) *Form.*—Nearly obovate with pointed apices at least on outer petals.

(4) *Arrangement.*—Regularly arranged, imbricated.

(5) *Petaloids in center.*—Few.

(6) *Persistence.*—Drop off cleanly.

(7) *Fragrance.*—Slight.

(8) *Lasting quality.*—Long lasting on plant and as cut flower.

REPRODUCTIVE ORGANS

A. Stamens, filaments and anthers:

*Arrangement and Color.*—Regularly arranged around styles. Color — filaments near 15A.

B. Pollen:

*Color.*—Near 17B.

C. Styles: Even, medium length, thin.

D. Stigmas:

*Color.*—Near 1C.

E. Hips: None observed.

PLANT

A. Form: Upright, compact.

B. Growth: Very vigorous.

*Height attained.*—About 12 to 15 inches.

C. Foliage: Compound 5 to 7 leaflets.

(1) *Size.*—Medium.

(2) *Quantity.*—Abundant.

(3) *Color.*—New foliage: Upper side — near 139C. Under side — near 144A. Old foliage: Upper side — near 137A. Under side — near 138B.

(4) *Shape.*—Oval, pointed.

(5) *Texture.*—Upper side is semi glossy; under side is matte.

(6) *Edge.*—Serrate.

(7) *Serration.*—Ordinary.

(8) Leaf stem.—Color — near 144A. Under side — near 144A to B.

(9) *Stipules.*—Fairly long, smooth.

(10) *Resistance to disease.*—Blackspot — Average. Mildew — Average. Rust — Average.

D. Wood:

(1) *New wood.*—Color — near 146B. Bark — smooth.

(2) *Old wood.*—Color — near 138A. Bark — smooth.

E. Thorns (prickles):

(1) *Thorns.*—Quantity (main stalk) — ordinary. On laterals from stalk very few. Form — long, thin, slightly downward curved. Length — medium. Color — near 181A. Position — irregular.

F. Winter hardiness: Needs protection in severe climates.

I claim:

1. A new and distinct variety of rose plant of the miniature rose class, substantially as shown and described, characterized particularly by attractive yellow and orange-red flowers of good form which are long lasting on the plant and after cutting.

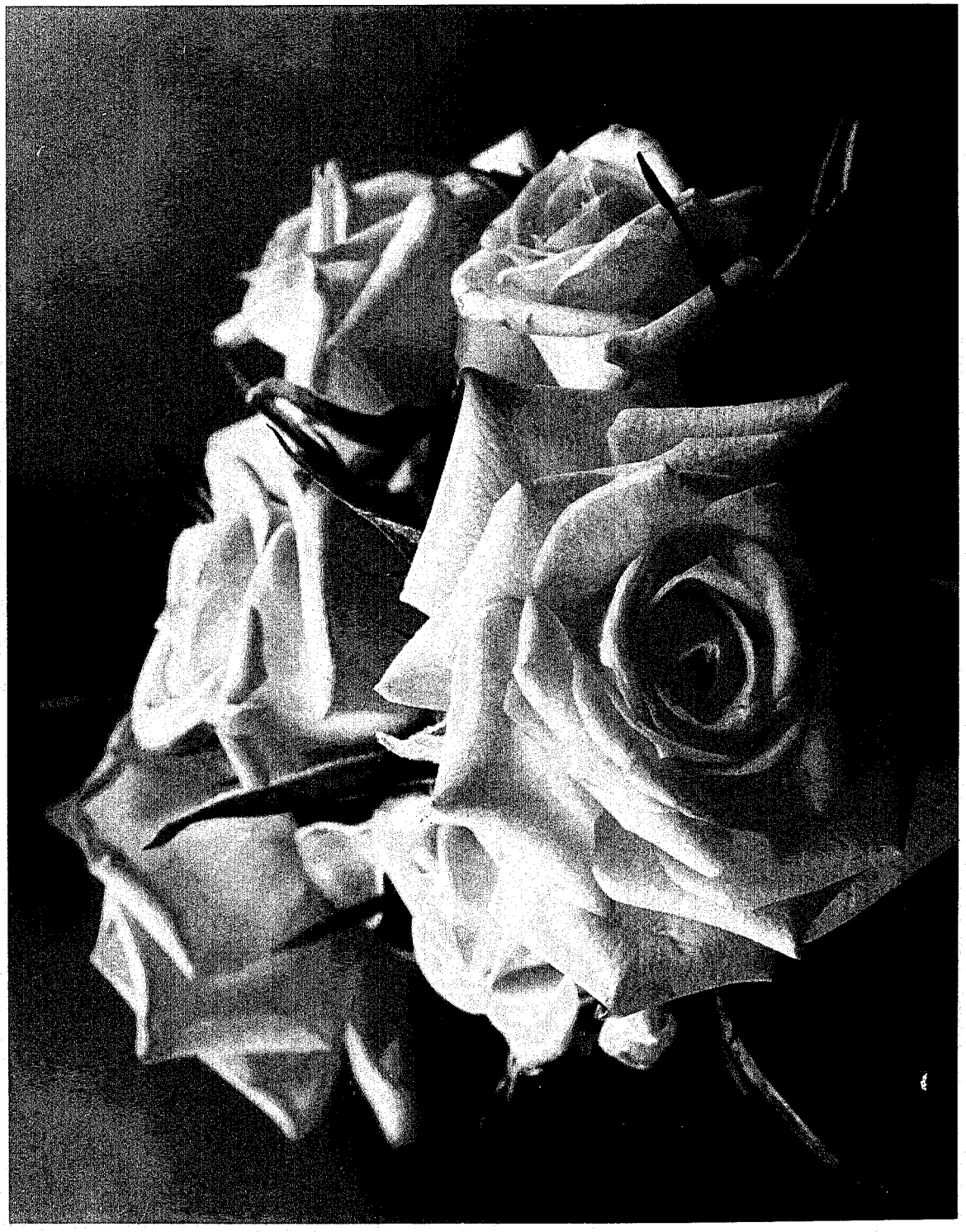

* * * * *